: US 11,041,140 B2
(45) Date of Patent: Jun. 22, 2021

(12) United States Patent
Pankratz et al.

(54) CELL CULTURE DEVICE

(75) Inventors: Gregory S. Pankratz, Middlesex, NY (US); Tom Nilsson, Birkerød (DK); John M. Staton, Medford, MA (US)

(73) Assignee: Nagle Nunc International Corporation, Rochester, NY (US)

( * ) Notice: Subject to any disclaimer, the term of this patent is extended or adjusted under 35 U.S.C. 154(b) by 1221 days.

(21) Appl. No.: 14/366,098

(22) PCT Filed: Oct. 12, 2011

(86) PCT No.: PCT/US2011/055968
§ 371 (c)(1),
(2), (4) Date: Nov. 11, 2015

(87) PCT Pub. No.: WO2012/051302
PCT Pub. Date: Apr. 19, 2012

(65) Prior Publication Data
US 2016/0115434 A1  Apr. 28, 2016

Related U.S. Application Data

(60) Provisional application No. 61/404,964, filed on Oct. 12, 2010.

(51) Int. Cl.
C12M 1/12 (2006.01)
C12M 3/00 (2006.01)
C12M 1/00 (2006.01)
(52) U.S. Cl.
CPC ............ *C12M 23/04* (2013.01); *C12M 21/08* (2013.01); *C12M 23/44* (2013.01); *C12M 23/58* (2013.01); *C12M 37/04* (2013.01)

(58) Field of Classification Search
CPC ...... C12M 23/04; C12M 23/44; C12M 37/04; C12M 21/08; C12M 23/58
See application file for complete search history.

(56) References Cited

U.S. PATENT DOCUMENTS 3,158,553 A    11/1964  Carski
5,240,854 A    8/1993   Berry et al.
(Continued)

FOREIGN PATENT DOCUMENTS

CN   101541428 A   9/2009
JP   4262775 A    9/1992
(Continued)

OTHER PUBLICATIONS

Ruiming, Chen, Article Entitled Animal Tissue Culture Technology and Its Application, p. 85, Key Points in Cell Culture, dated Dec. 31, 1991 (1 page).

(Continued)

*Primary Examiner* — Gautam Prakash
(74) *Attorney, Agent, or Firm* — Workman Nydegger

(57) ABSTRACT

A cell culture device (10) of the cultivation of cells. The cell culture device (10) includes a plurality of trays (12a, 12b, 12c, 12d), each tray (12a, 12b, 12c, 12d) having a cell growth surface (20) and at least one wall (22, 24) extending upwardly from the cell growth surface (20). The at least one wall (22, 24) is configured to receive an additional tray thereon. A ratio of the number of the plurality of trays (12a, 12b, 12c, 12d) per a height dimension of the plurality of trays (12a, 12b, 12c, 12d) is greater than or equal to about 1 tray per 12 mm.

6 Claims, 4 Drawing Sheets

(56) References Cited

U.S. PATENT DOCUMENTS

| | | | |
|---|---|---|---|
| 5,439,142 A * | 8/1995 | Robertson et al. | A47G 19/12 222/164 |
| 5,958,778 A * | 9/1999 | Kidd | B01L 3/5021 422/548 |
| 6,569,675 B2 | 5/2003 | Wall et al. | |
| 7,867,761 B2 | 1/2011 | Esser et al. | |
| 2002/0100739 A1 | 8/2002 | Day et al. | |
| 2004/0072347 A1 | 4/2004 | Schuler et al. | |
| 2007/0065933 A1 | 3/2007 | Esser et al. | |
| 2009/0298163 A1 | 12/2009 | Bennett et al. | |

FOREIGN PATENT DOCUMENTS

| | | |
|---|---|---|
| JP | 5501953 A | 4/1993 |
| JP | 2004535829 A | 12/2004 |
| WO | 9205243 A1 | 4/1992 |
| WO | 02057159 A1 | 7/2002 |
| WO | 03012081 A1 | 2/2003 |
| WO | 2005035728 A2 | 4/2005 |
| WO | 2007015770 A1 | 2/2007 |
| WO | 2008/030961 A1 | 3/2008 |
| WO | 2010/008566 A3 | 1/2010 |

OTHER PUBLICATIONS

Ruiming, Chen, English Translation of Article entitled Animal Tissue Culture Technology and Its Application, p. 85, Key Points in Cell Culture, dated Dec. 31, 1991 (1 page).
Chinese Patent Office, Office Action, Application No. 201180058584. 2, dated Nov. 10, 2015 (9 pages).
Chinese Patent Office, English Translation of Office Action, Application No. 201180058584.2, dated Nov. 10, 2015 (8 pages).
ISA/US, International Search Report and Written Opinion of the International Searching Authority, International Application No. PCT/US2011/055968, dated Jan. 12, 2012 (7 pages).
The International Bureau of WIPO, International Preliminary Report on Patentability, International Application No. PCT/US2011/055968, dated Apr. 25, 2013 (6 pages).
Corning Incorporated, CellCube Culture System, User's Manual, Rev. V1.02, Corning Cat. No. 3143, 2011 (68 pages).
Corning Incorporated, Corning CellSTACK Culture Chambers, Instructions for Use, POD CLS-BP-007 REV5, 2007 (4 pages).
Thermo Fisher Scientific Inc., Thermo Scientific Nunc Cell Factory Brochure, Instructions for use: CF1, CF4, CF10 and CF40, dated 2010 (2 pages).
Corning Incorporated, Corning CellBIND Surface CellSTACK Culture Chambers, CLS3320-10 chamber, surface treatment Corning CellBIND, retrieved from http://www.sigmaaldrich.com/catalog/ProductDetail on Aug. 9, 2011 (1 page).
Corning Incorporated, Corning CellSTACK Culture Chambers, CLS3272-40 chamber, surface treatment TC-Treated, retrieved from http://www.sigmaaldrich.com/catalog/ProductDetail, retrieved on Aug. 9, 2011 (1 page).
Canadian Patent Office, Office Action, Application No. 2,814,406, dated Jun. 20, 2017 (4 pages).
Chinese Patent Office, Second Office Action and Search Report, Application No. 201180058584.2, dated Feb. 16, 2015 (8 pages).
Chinese Patent Office, English Machine Translation of Second Office Action and Search Report, Application No. 201180058584.2, dated Feb. 16, 2015 (7 pages).
Japanese Patent Office, English Translation of Office Action, Japanese Patent Application No. 2013-533972, dated Apr. 20, 2015 (4 pages).
Japanese Patent Office, Office Action, Japanese Patent Application No. 2013-533972, dated Apr. 20, 2015 (4 pages).
European Patent Office, Extended European Search Report, Application No. 11833337.6, dated Jan. 16, 2017 (12 pages).
Japanese Patent Office, Office Action, Japanese Patent Application No. 2016-134838, dated May 22, 2017 (6 pages).
Chinese Patent Office, Notification of Reexamination, Application No. 201180058584.2, dated Jul. 21, 2017 (18 pages).
Corning Life Sciences, CorningTM HYPERFlaskTM Cell Culture Vessel, XP-002762300, retrieved from http://www.level.com.tw/html/ezcatfiles/vipweb20/img/img/21657/an_HYPERFlask_protocol.pdf, retrieved on Sep. 23, 2016, dated Feb. 4, 2008 (4 pages).
European Patent Office, Supplementary Partial European Search Report, Application No. EP11833337, dated Oct. 14, 2016 (8 pages).
Mexican Institute of Industrial Property, Second Substantive Examination Requirement IPL, Application No. MX/a/2013/004171, dated Oct. 6, 2017 (4 pages).
Japanese Patent Office, Second Office Action, Japanese Patent Application No. 2016-134838, dated Apr. 9, 2018 (7 pages).
Brazilian Patent Office, Technical Examination Report and Search Report, Application No. BR112013008581-9, dated Jun. 7, 2018 (17 pages).
Canadian Patent Office, Office Action, Application No. 2,814,406, dated Dec. 4, 2018 (3 pages).
Corning Life Sciences: "Growing More Cells: A Simple Guide to Small Volume Cell Culture Scale Up" (published Mar. 2008), [retrieved from the internet Jan. 23, 2019]< url:< a=""href="https://www.corning.com/media/worldwide/cls/documents/cc_scale_up_guide.pdf>">https://www.corning.com/media/worldwide/cls/documents/cc_scale_up_guide.pdf.</url:>.

* cited by examiner

CELL CULTURE DEVICE

The present application claims the filing benefit of U.S. Provisional Application Ser. No. 61/404,964, filed Oct. 12, 2010, the disclosure of which is incorporated herein by reference in its entirety.

FIELD OF THE INVENTION

The present invention relates generally to cell culture devices and, more specifically, to a stack of communicating trays for culturing cells.

BACKGROUND OF THE INVENTION

Cell culture systems, including stacked trays, are useful for large-scale cell cultivation and have become popular as an alternative to conventional roller bottles, bioreactors, and the like. Exemplary stacked tray systems include the NUNC CELL FACTORY system (Nunc A/S, Roskilde, Denmark), the Corning CELLSTACK (Corning Inc., Lowell, Mass.) and the Millipore MILLICELL HY flasks (Millipore Corp., Billerica, Mass.). Such systems include one or more culture trays, each with a larger cell growth surface area as compared to the conventional devices, e.g., a surface area generally of at least 200 $cm^2$.

For example, the NUNC CELL FACTORY system includes a stack of trays, wherein each tray is approximately 335 mm in length and 205 mm in width to provide a cell growth surface area of approximately 632 $cm^2$. Such trays are commercially-available as individual trays or in stacks that generally consist of two, four, ten, or forty trays. The trays comprising a stack are typically attached via ultrasonic welding. These systems further include a height of about 14.65 mm and are recommended to contain about 200 mL of the growth culture medium. Given the culture surface area per tray of about 632 $cm^2$, the about 200 mL of growth culture medium would have a height of about 1.5 mm within the tray and the remaining height, about 12.6 mm (after accounting for the thickness of the bottom wall, e.g., approximately 0.5 mm) is considered head space.

Generally, the stack of trays is equipped with a gas exchanger having a gas conduit providing fluid communication between the trays and at least one processed aperture for venting the stack. The gas exchanger provides a fast and substantially uniform distribution of gas to all trays within the stack.

Although stacked tray culture systems have been widely used, particularly for large-scale cultivation of cultured cells, the stacked trays occupy a significant amount of incubator, laboratory, and storage space, particularly when purchased as stacks include ten or more trays. Thus, it would be advantageous to increase the total growing surface area per stack without increasing the height or footprint of the stacks. An increase in growing surface area would reduce the number of stacked tray systems needed to provide a given surface area, and reduce the incubator, laboratory, or storage space occupied by the stacks.

However, it has been conventional belief that proper growth of cells required a significant air space volume above each cell growth surface area, for example, more than 3 mm (in a vertical dimension) of air space above the cell culture. Alternatively, conventional devices have incorporated bottom surface materials having a significant oxygen and/or carbon dioxide permeability (e.g., silicone or 3 mil biaxially-oriented polystyrene film). Thus, optimizing the total growing surface area without additional trays or increases the tray footprint and provided a significant challenge to the space problem.

SUMMARY OF THE INVENTION

The present invention overcomes the foregoing problems and other shortcomings, drawbacks, and challenges of conventional cell culture devices comprising stackable trays. While the invention will be described in connection with certain embodiments, it will be understood that the invention is not limited to these embodiments. To the contrary, this invention includes all alternatives, modifications, and equivalents as may be included within the spirit and scope of the present invention According to an embodiment of the invention, a cell culture device for the cultivation of cells. The cell culture device includes a plurality of trays, each tray having a cell growth surface and at least one wall extending upwardly from the cell growth surface. The at least one wall is configured to receive an additional tray thereon. A ratio of the number of the plurality of trays per a height dimension of the plurality of trays is greater than or equal to about 1 tray per 12 mm.

According to other another embodiment of the invention, a method for preparing a stack of trays for the cultivation of cells includes positioning a first tray in a stacked position relative to a second tray. The first and second trays include side walls, end walls, a groove defined in the side walls and end walls, a bottom, and a tongue depending from the bottom. In the stacked position, the groove of the first tray receives the tongue of the second tray.

Still another embodiment of the present invention is directed to a cell culture tray. The cell culture tray includes a tray bottom having an upwardly facing cell growth surface and a downwardly facing surface. At least one wall extends upwardly from the cell growth surface and includes a top edge. At least one venting port extends through the tray bottom. The at least one wall includes a groove extending downwardly from the top edge and defining an inner groove wall and an outer groove wall, and the downwardly facing surface includes a tongue depending therefrom. The groove is configured to receive a tongue of another tray positioned above the cell culture tray, and the at least one venting port is configured to align with the at least one venting portion of the another tray.

The above and other objects and advantages of the present invention shall be made apparent from the accompanying drawings and the descriptions thereof.

BRIEF DESCRIPTION OF THE DRAWINGS

The accompanying drawings, which are incorporated in and constitute a part of this specification, illustrate embodiments of the invention and, together with the general description given above and the detailed description of the embodiments given below, serve to explain the principles of the present invention. In the figures, corresponding or like numbers or characters indicate corresponding or like structures.

DETAILED DESCRIPTION OF THE INVENTION

Figure 1:
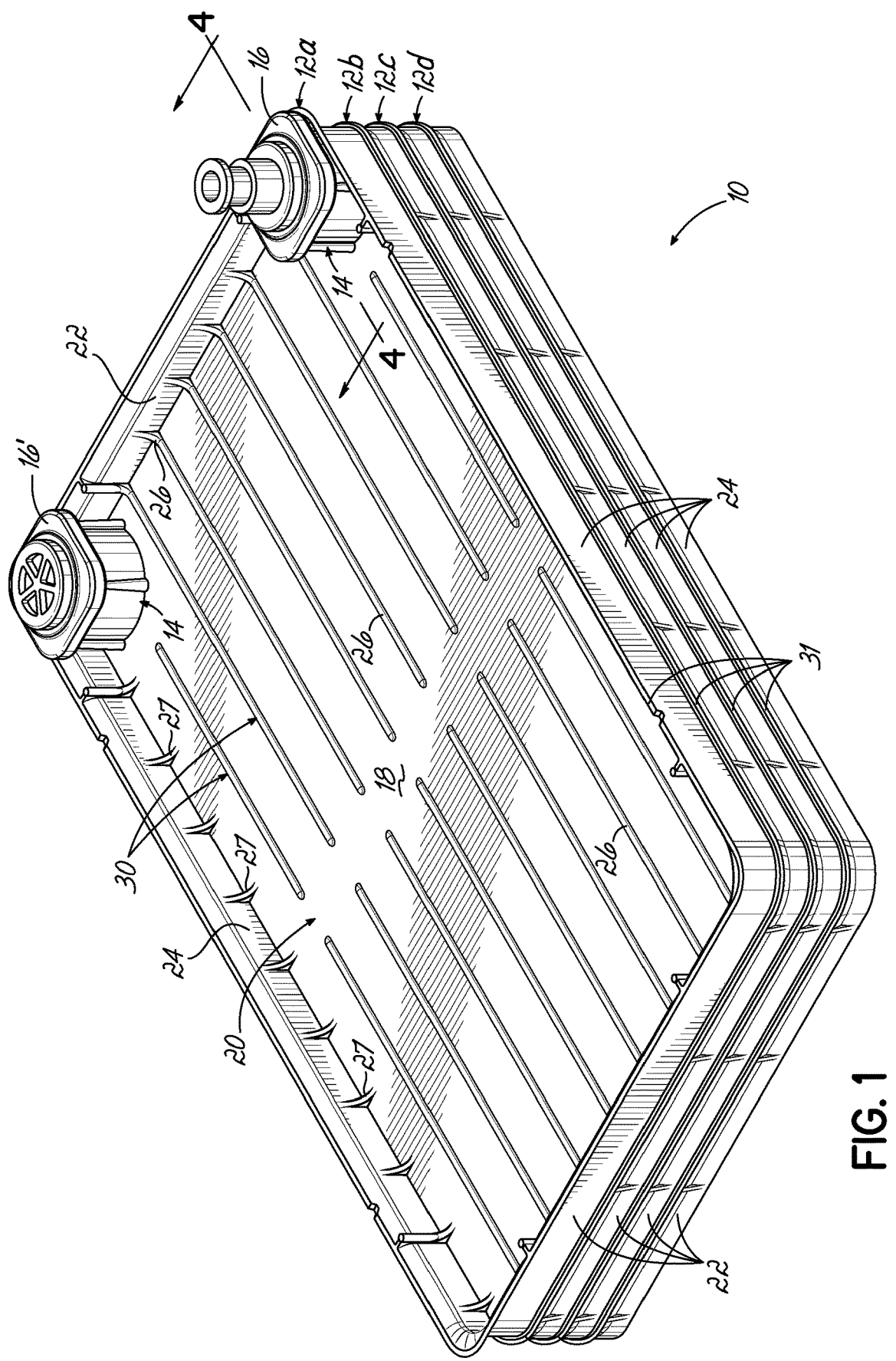
FIG. 1 is a perspective view showing a cell culture device in accordance with one embodiment of the present invention.

Referring now to the figures and, in particular, to FIG. 1, a cell culture device 10 ("device" 10) in accordance with one embodiment of the present invention is described. The device is comprised of a plurality of trays 12a, 12b, 12c, 12d, each configured for the cultivation of cells. Each tray 12a, 12b, 12c, 12d is stacked vertically with respect to another tray 12a, 12b, 12c, 12d. Although the number of trays 12a, 12b, 12c, 12d may vary, the illustrative embodiment includes four.

Figure 2:
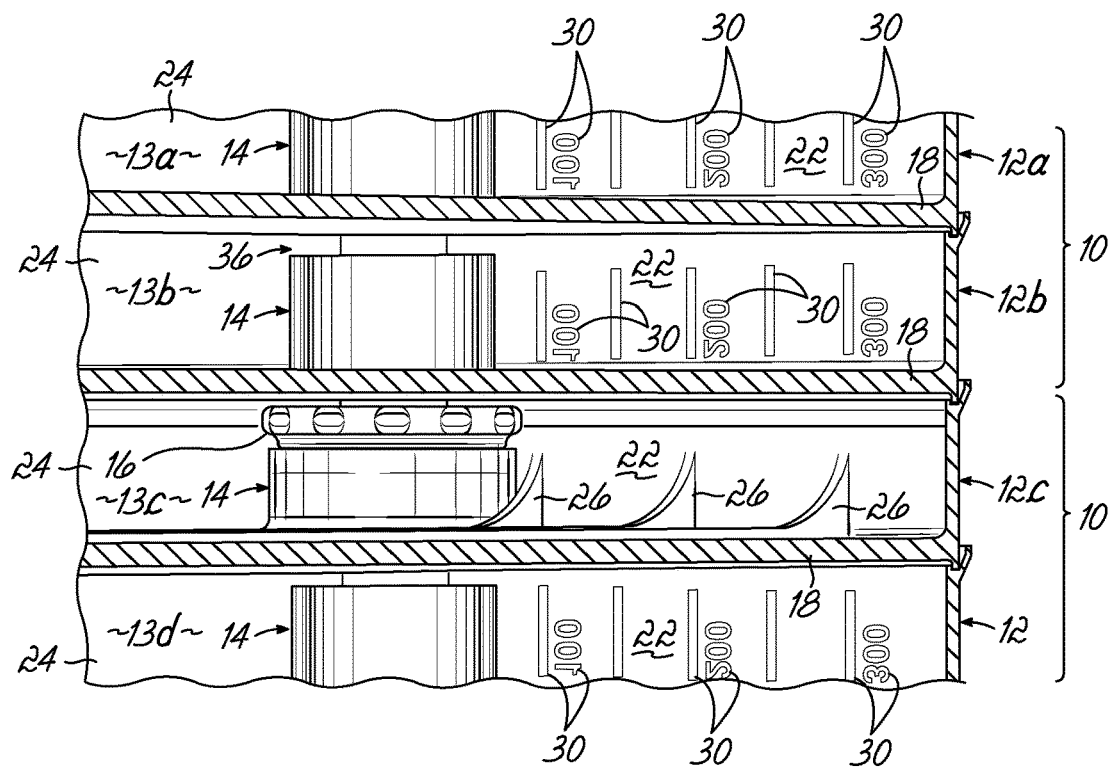
FIG. 2 is a cross-sectional view of a stack of two cell culture devices, each of the cell culture devices being similar to the cell culture device of FIG. 1.

The trays 12a, 12b, 12c, 12d are configured to be in fluid communication with each other and, thus, provide a total device volume that is the sum of each volume 13a, 13b, 13c, 13d (FIG. 2) of the respective tray 12a, 12b, 12c, 12d. Gas exchange between the total device volume and the environment outside the device 10 may occur via one or more venting ports 14. A closure 16, 16" may be associated with each venting port 14 of the tray 12d positioned at a top of the stack (or in the tray if only an individual tray is desired). In some embodiments, the closure 16 may include a low profile shape so as to facilitate the stacking of two or more devices 10 as is shown in FIG. 2. An example of a low profile closure 16, 16 suitable for use with the device 10 is described in U.S. patent application Ser. No. 14/366,173, entitled VENTABLE CLOSURE WITH PORT, filed on even date herewith and published as US Publication No. 2015/0203258 on Jul. 23, 2015, the disclosure of which is incorporated herein by reference in its entirety.

Referring still to FIG. 1, each tray 12a, 12b, 12c, 12d includes a floor or bottom 18 defining a growth surface 20 and at least one wall extending upwardly from the bottom 18 of the tray 12a, 12b, 12c, 12d. While the trays 12a, 12b, 12c, 12d may incorporate any suitable shape, including, for example, rectangular, square, round, circular, oblong, elliptical, polygonal, or trapezoidal, the illustrated device 10 is substantially rectangular and includes two substantially parallel end walls 22 and two substantially parallel side walls 24 extend upwardly from the bottom 18 of the tray 12. When stacked, the bottom 18 of one tray may provide a top or cover for an immediately adjacent tray positioned below the one tray. Thus, the top tray 12d may remain open to the environment outside the device 10 or, alternatively, a separate cover piece (not shown) may be used.

The trays 12a, 12b, 12c, 12d may include one or more features designed to provide a particular benefit to the device 10; however, the features may be incorporated in any combination and all or some may not be included in any one particular embodiment. For example, each tray 12a, 12b, 12c, 12d may be reinforced with one or more reinforcement ribs 26 extending at least partially in a longitudinal direction of the bottom 18 of the tray 12a, 12b, 12c, 12d. The reinforcement ribs 26 may further extend upwardly along the end walls 22. In some embodiments, the reinforcement ribs 26 may extend along a substantial portion of the bottom 18, providing structural support to the bottom 18. In some embodiments, the sidewalls 24 may also comprise reinforcement ribs 27, which may be shaped in a manner that is similar to the reinforcement ribs 26 (e.g., extending along the bottom 18 of the tray 12a, 12b, 12c, 12d) or, as shown, being primarily positioned at the junction between the bottom 18 and the side walls 24.

As shown in FIG. 2, at least the top tray 12d in the device 10 may include one or more indicia, e.g., lines or other marks 30, indicative of the volume of the contents of each tray 12a, 12b, 12c, 12d and/or the volume of the contents the device 10, in toto. Such marks 30 may be located on either or both of the side wall 24 or the end wall 22. In some embodiments, the reinforcement members 26 may also comprise, or be co-extensive with, the marks 30, thereby providing a volume-indicating function as well as structural reinforcement. While the marks 30 as shown in FIG. 2 are accompanied by labels indicating a volume amount, such as, "100", "200", "300", it would be understood that the labels are not required.

Figure 3:
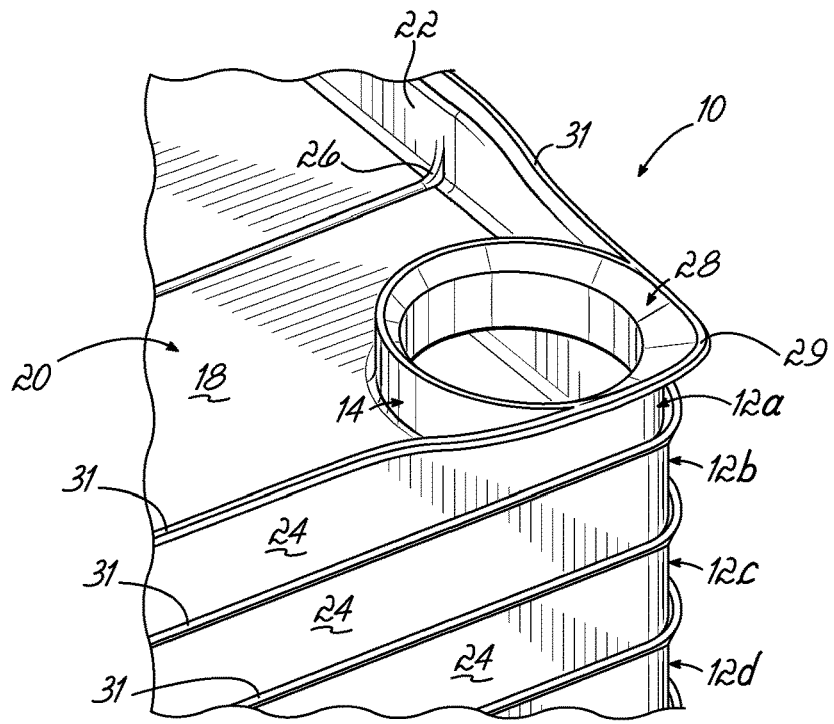
FIG. 3 is an enlarged perspective view of a port of the cell culture device of claim 1.

Referring to FIG. 3, the top-most tray may be somewhat different than the other trays 12b, 12c, 12d comprising the stack as the top-most tray 12a may require structural features for performing one or more particular functions. For example, the venting ports 14 of the top-most tray 12d may include a pour spout 28. In that regard, the pour spout 28 may be formed as a lip 29 extending laterally away from a rim 31 defining a top edge of the walls 22, 24 of the tray 12d. Accordingly, and with the closure 16 removed from the venting port 14, the pour spout 28 may be configured to drain a fluid from the device 10.

Figure 4:
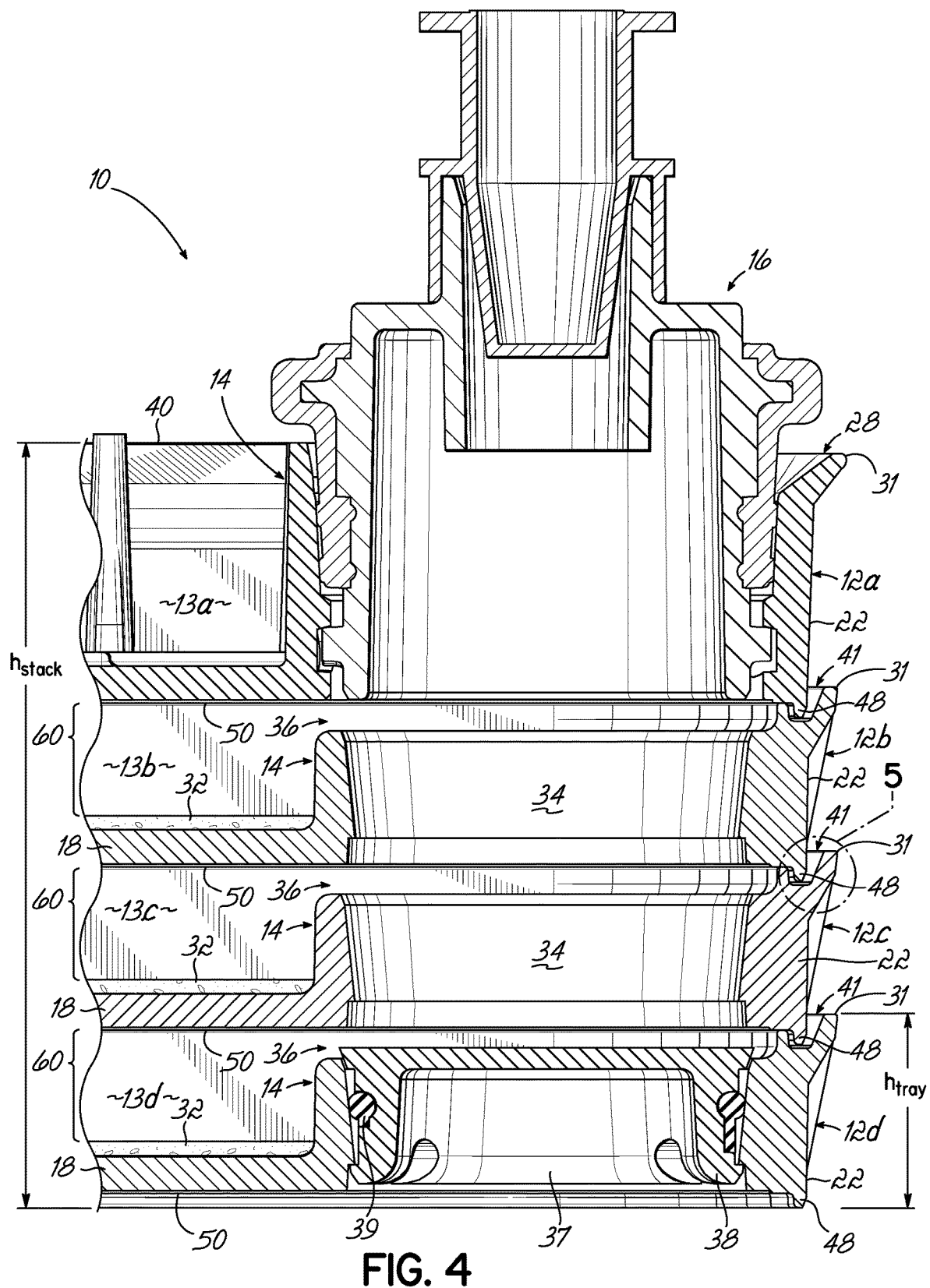
FIG. 4 is a cross-sectional view of a portion of the cell culture device of FIG. 1, taken along the line 4-4 in FIG. 1.

The trays 12a, 12b, 12c, 12d may be molded using a thermoplastic material, including, for example, polystyrene. Depending upon the material used, the thickness of the tray bottom 18 may vary but should be sufficient to prevent significant bowing of the bottom 18 when the device 10 is filled with an appropriate volume of culture medium 32 (FIG. 4). For polystyrene, a thickness of about 0.5 mm is recommended for trays having a culture surface area of about 632 cm$^2$ and configured to hold about 200 mL to about 300 mL of culture medium 32 (FIG. 4).

In some embodiments, the device 10 may constructed from a material that withstands sterilization, including, for example, sterilization by irradiation (beta or gamma radiation), steam autoclave, ethylene oxide, chemical disinfectants, or dry heat sterilization. In these or other embodiments, the device 10 may be made from a thermoplastic material and/or from a material that is formed, for instance, by injection molding. Examples of materials that are suitable for use in the present context include, for example, polyethylene, polypropylene, polystyrene, polycarbonate, polyurethane, polysulfone, polymethylpentene, polymethylmetacrylate, polyethyleneterepthtalate, polytetrafluoroethylene, or ABS (acrylonitrilbutadiene styrene). However, the examples given here only exemplary in nature a person skilled in the art would readily appreciate how to select other materials suitable for use in constructing the device.

With reference now to FIG. 4, the lower trays 12b, 12c, 12d are shown as including a volume of a liquid, such as a cell culture medium 32. The lower trays 12b, 12c, 12d are generally in fluid communication with one another via the venting ports 14 that, being a portion of a lower tray 12b, 12c, 12d, lack a closure 16 and thus define a fluid path or channel 34 between and among the lower trays 12b, 12c, 12d. An opening 36 is formed between the venting port 14 of each tray 12b, 12c, 12d and the above and immediately adjacent tray 12a, 12b, 12c and provides fluid communication between the volumes 13b, 13c, 13d of the trays 12b, 12c, 12d. In this way, gases may be exchanged between the cell cultures within each tray 12b, 12c, 12d and provides for a more uniform growth environment. The channel 34 has a lower-most end 37 that opposes the closure 16 and that is within the lower-most tray 12d. In that regard, the lower-most tray 12d may include a stopper 38 within the venting port 14 to seal the lower-most end 37 of the channel 34 and to prevent inadvertent loss of the culture medium 32 and/or reduce the risk of microbial contamination. The stopper 38 may include one or more ribs, at least one thread, an o-ring 39, or other devices, with or without adhesives, for forming a seal with the venting port 14.

Referring still to FIG. 4, the device 10 may be constructed by joining adjacent ones of the trays 12a, 12b, 12c, 12d comprising the stack, which may include, for example, laser welding, ultrasonic welding, solvent bonding, or adhesive bonding (gluing).

Figure 5:
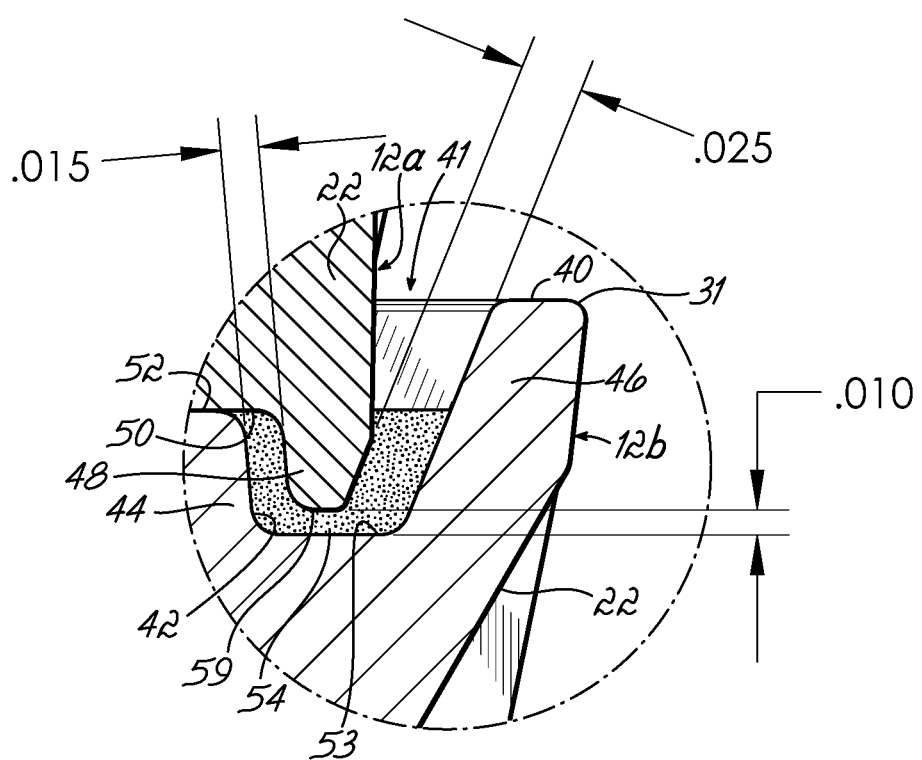
FIG. 5 is an enlarged view of a joint between successive trays encircled 5 in FIG. 4, the trays comprising the cell culture device of FIG. 1

Adhesive bonding offers production advantages, for example, by reducing the number of stacks rejected due to failed attachment via welding. Thus, to further enhance the effectiveness of adhesive bonding, the trays 12a, 12b, 12c, 12d may includes various structural elements that facilitate stacking, alignment, and attachment. More specifically, and with reference now to FIGS. 4 and 5, the trays 12a, 12b, 12c, 12d may include a joint 41, namely, a tongue-in-groove joint, at the point of contact between adjacent ones of the trays 12a, 12b, 12c, 12d. FIG. 5 illustrates, in more detail, one such embodiment of the tongue-in-groove joint 41. In particular, each tray 12b, 12c, 12d (not including the top-most tray 12a as this tray includes the pour spout 28) includes an upper surface 40 on each end wall 22 and side wall 24 and positioned proximate the rim 31. A groove 42 extends downwardly into the walls 22, 24 and may extend around at least a portion of the upper periphery of the walls 22, 24 of each tray 12b, 12c, 12d. The groove 42 defines an inner groove wall 44 and an outer groove wall 46, wherein the inner groove wall 44 may be generally shorter than the outer groove 46. The groove 42 has a shape and size that is configured to receive a tongue 48 that depends downwardly from a bottom outer surface 50 of the tray 12a, 12b, 12c, 12d. In some embodiments, the tongue 48 may extend around at least a portion of the lower periphery of each tray 12a, 12b, 12c, 12d. Thus, and when a first tray 12a, 12b, 12c is placed above and positioned onto a second 12b, 12c, 12d, the groove 42 of second tray 12b, 12c, 12d receives the tongue 48 of the first tray 12a, 12b, 12c, i.e., the above and immediate adjacent tray 12a, 12b, 12c. In some embodiments, the tongue 48 may be a co-extensive with the walls 22, 24; otherwise, the tongue 48 may be inwardly offset from the walls 22, 24 and extending from the bottom outer surface 50.

The inner groove wall 44 may have an upper surface 52 that is configured to receive and be adjacent to the bottom outer surface 50 of the above and immediately adjacent tray. This contact is configured to resist movement of an adhesive from the groove 42 and into the volume 13b, 13c, 13d of the trays 12b, 12c, 12d. In some embodiments, the tongue 48 may have a lateral width dimension that is smaller than a lateral width dimension of the groove 42 and so the tongue 48 may reside within, but not completely fill, the groove 42. In some embodiments, the tongue 48 may be configured so as to not contact the inner groove wall 44, the outer groove wall 46, or a bottom wall 53 of the groove 42. Spacing the tongue 48 away from these walls 44, 46, 53 defines a space between the tongue 48 and the groove 42 configured to receive an adhesive 54. The shape and size of the inner and outer groove walls 44, 46 is configured to spread the adhesive upwardly and around the tongue 48 when the trays 12a, 12b, 12c, 12 are in the stacked arrangement. Spreading the adhesive in this way increases the surface area for adhesive bonding. While the spacing may vary, in some embodiments, the spacing between the tongue 48 and the inner groove wall 44 may be approximately 0.015 inches (0.381 mm), the spacing between the tongue 48 and the outer groove wall 46 may be approximately 0.025 inches (0.635 mm), and the spacing between the tongue 48 and the bottom of the groove 42 may be approximately 0.010 inches (0.254 mm).

To construct the device 10, and once the trays 12a, 12b, 12c, 12d are stacked, a small volume of adhesive 54 is directed into the groove 42. The contact angle of the adhesive 54 relative to the wall surfaces of the groove 42, and/or the viscosity of the adhesive, cause the adhesive to spread and to fill the spaces between the tongue 48 and the inner groove wall 44, the outer groove wall 46, and the bottom wall 53, as was discussed in detail above. While any suitable adhesive known to those of ordinary skill in the art for bonding plastics may be used, suitable adhesives may include those having a low cytotoxicity or, more preferably, an adhesive considered non-cytotoxic. Examples of suitable adhesives useful for making the present invention include, but are not limited to, UV/light cured urethane-acrylic adhesives, oxygen/moisture-cured or UV/light-cured cyano-acrylate adhesives, self-curing epoxies, and UV/light-cured vinyl acrylamide-based adhesives. Such adhesives may include poly(N,N-dimethyl acrylamide, poly(isobornyl methacrylate), poly(isobornyl acrylate), or a combination thereof.

The device 10 of FIG. 1, constructed in a manner as describe above, may offer several advantages. For one, the strict tolerances as well as the shape and size of the relative surfaces of the tongue-in-groove joint 14 enable manufacturing to be performed by automated machines and according to efficient manufacturing processes. Automation of manufacturing methods may provide consistency in product manufacture and a reduction of manufacturing errors. Moreover, the tongue-in-groove joint 41 may provide consistency as to the relative positioning of one tray 12a, 12b, 12c, 12d with respect to an adjacent tray 12a, 12b, 12c, 12d, thereby reducing the potential for positioning errors, which may otherwise propagate in a stack comprising a large number of trays, for example, a stacks having twenty, forty, or more trays. Also, the shape and size of the inner groove wall 44 relative to the bottom surface 50 of the above and immediately adjacent tray contain the adhesive generally to the tongue-in-groove 41 joint and resists leakage into the volume 13a, 13b, 13c, 13d of the trays 12a, 12b, 12c, 12d and reduces the risk of the associated contamination.

In accordance with various embodiments of the present invention, the height of the device 10 may be reduced for providing a larger cell growth surface area per unit height of the device 10. As such, and with reference again to FIG. 4, each tray 12a, 12b, 12c, 12d has a height dimension, $h_{tray}$, that extends from a bottom edge 59 of the tongue 48 to the rim 31 of the same tray 12a, 12b, 12c, 12d. The device 10 comprising a stack of trays 12 extends upwardly from the bottom edge 59 of the tongue 48 of the lower most tray 12d to the rim 31 of the topmost tray 12a (excluding any closure 16, which is removable from the stack 10), which defines a total device height, $h_{stack}$. The stack height, $h_{stack}$, may be approximately equal to the sum of the component tray heights, $h_{tray}$, comprising the stack; however, the total device height, $h_{stack}$, may, in reality, be slightly smaller than the straight sum because of the overlap of the trays 12a, 12b, 12c, 12d in the region of the joint 41.

During use, and when the culture medium 32 is contained within the volumes 13b, 13c, 13d of the trays 12b, 12c, 12d, a head space 60 is defined as being the space located the culture medium 32 contained within the tray 12b, 12c, 12d and the bottom outer surface 50 of the above and immediately adjacent tray 12a, 12b, 12c.

The tray height, $h_{tray}$, of each tray 12a, 12b, 12c, 12d may be reduced, principally, by reducing the height of the walls 22, 24. Surprisingly, the amount of head space 60 may be reduced without detrimental effects to the growth rate and health of the cell culture. Said another way, it was discovered that the tray height, $h_{tray}$, may be reduced to range from about 12 mm to about 6 mm without detrimentally affecting the cell culture growth and health. For example, a tray having a growth surface area of about 632 $cm^2$ and a tray height ranging from about 7.5 mm to about 9.5 mm may accommodated up to 300 mL of culture medium per tray while providing adequate headspace for gas exchange and cell growth. With such a reduction in the tray height, a device comprising a stack of sixty trays in accordance with one or more embodiments of the present invention may have, for example, a device height that is substantially equivalent to the device height of a device comprising forty conventional trays. Similarly, a device comprising a stack of fifteen trays in accordance with one or more embodiments of the present invention may have a device height that is substantially equivalent to the device height of a device comprising a stack of conventional trays. The reduction in height yields substantial savings in terms of space and resources. Thus, the total cell growing surface area of a device in accordance with an embodiment of the present invention is increased as compared to the total cell growing surface area of a conventional device of similar height Accordingly, a device 10 comprising a stack of trays 12 may be characterized in terms of a ratio of the number of trays per the millimeter of device height. In some embodiments, the ratio may range from about 1:12 to about 1:6. In some embodiments, the ratio may be about 1:9.5. In still other embodiments, the ratio may be 1:6 or 1:7.5

The devices according to the various embodiments herein may include trays having any combination of lengths and widths and, therefore, provide a wide range of growing surface areas. Some embodiments may include trays having a surface area ranging from approximately 200 $cm^2$ and 700 $cm^2$, but sizes outside this range are also contemplated. Furthermore, the devices may include a shape and/or size configured to be handled via mechanical (robotic) instruments.

While the invention has been illustrated by the description of embodiments thereof, and while the embodiments have been described in considerable detail, it is not intended to restrict or in any way limit the scope of the appended claims to such detail. Additional advantages and modifications will readily appear to those skilled in the art. Therefore, the invention in its broadest aspects is not limited to the specific details shown and described. The various features disclosed herein may be used in any combination necessary or desired for a particular application. Consequently, departures may be made from the details described herein without departing from the spirit and scope of the claims which follow.

What is claimed is:

1. A cell culturing device, comprising:
   a plurality of stacked trays, each tray having a bottom defining a cell growth surface and at least one wall extending upwardly from the bottom, each bottom having an outer bottom surface, the plurality of stacked trays comprising a top tray that is stacked on top of a plurality of lower trays that are stacked, the bottom and the at least one wall of the plurality of lower trays defining, in combination with the bottom outer surface of an immediately adjacent tray of the plurality of stacked trays, a volume configured to contain the cell growth surface and a volume of growth medium, including a headspace for gas exchange positioned above the volume of growth medium and below the bottom outer surface of the immediately adjacent tray of the plurality of stacked trays, the at least one wall being configured to receive the immediately adjacent tray thereon;
   at least one of the trays of the plurality of lower trays having a first and a second venting port extending upwardly from the bottom, each venting port defining a channel passing through the bottom and being in fluid communication with at least one immediately adjacent tray, the venting ports each defining an opening between the venting port and the bottom outer surface of an immediately adjacent tray located above the at least one tray of the plurality of lower trays so that an open fluid path extends from the channel of the venting ports to the volume of growth media;
   wherein the top tray comprises a vent port extending upwardly from the bottom thereof and a rim defining a top edge of the top tray, a lip extends laterally away from the rim at a location adjacent to the vent port to define a pour spout for draining a fluid from the cell culturing device,
   wherein a ratio of a number of the plurality of stacked trays per a height dimension of the plurality of stacked trays is greater than or equal to 1 tray per 12 mm,
   further comprising:
   the plurality of stacked trays being connected by a tongue-in-groove joint wherein each of the plurality of stacked trays include a bottom surface and a tongue depending downwardly from the bottom surface and around at least a portion of a lower periphery of each tray; and
   the at least one wall of each of the plurality of lower trays comprises side walls, end walls, and a groove extending around at least a portion of an upper periphery of each of the plurality of lower trays, the groove being defined in the side walls and end walls, the groove defining an inner groove wall having an upper face and an outer groove wall having an upper face, the groove terminating at an inner bottom face that extends between the inner groove wall and the outer groove wall, the inner groove wall having a height extending between the inner bottom face of the groove and the upper face of the inner groove wall that is shorter than a height of the outer groove wall extending between the inner bottom face of the groove and the upper face of the outer groove wall.

2. The cell culturing device of claim 1, wherein the ratio is less than or equal to 1 tray per 6 mm.

3. The cell culturing device of claim 1, wherein the tongue is smaller than the groove.

4. The cell culturing device of claim 1, further comprising an adhesive bonding adjacent trays.

5. A cell culturing device, comprising:
   a plurality of stacked trays, each tray having a bottom defining a cell growth surface and at least one wall extending upwardly from the bottom, each bottom having an outer bottom surface, the plurality of stacked trays comprising a top tray that is stacked on top of a plurality of lower trays that are stacked, the bottom and the at least one wall of the plurality of lower trays defining, in combination with the bottom outer surface of an immediately adjacent tray of the plurality of stacked trays, a volume configured to contain the cell growth surface and a volume of growth medium, including a headspace for gas exchange positioned above the volume of growth medium and below the bottom outer surface of the immediately adjacent tray of the plurality of stacked trays, the at least one wall being configured to receive the immediately adjacent tray thereon;

at least one of the trays of the plurality of lower trays having a first and a second venting port extending upwardly from the bottom, each venting port defining a channel passing through the bottom and being in fluid communication with at least one immediately adjacent tray, the venting ports each defining an opening between the venting port and the bottom outer surface of an immediately adjacent tray located above the at least one tray of the plurality of lower trays so that an open fluid path extends from the channel of the venting ports to the volume of growth media;

wherein the top tray comprises a vent port extending upwardly from the bottom thereof and a rim defining a top edge of the top tray, a lip extends laterally away from the rim at a location adjacent to the vent port to define a pour spout for draining a fluid from the cell culturing device, wherein a ratio of a number of the plurality of stacked trays per a height dimension of the plurality of stacked trays is greater than or equal to 1 tray per 12 mm, further comprising:

a tongue depending downwardly from the bottom outer surface of each of the plurality of stacked trays so that the tongue extends around at least a portion of a lower periphery of each the plurality of stacked trays;

the at least one wall of each of the plurality of lower trays extending around at least a portion of an upper periphery of each of the plurality of lower trays, each at least one wall of each of the plurality of lower trays comprising:

an inner groove wall terminating at an upper face;

an outer groove wall terminating at an upper face; and a groove recessed into the at least one wall between inner groove wall and the outer groove wall, the groove terminating at an inner bottom face that extends between the inner groove wall and the outer groove wall, the inner groove wall having a height extending between the inner bottom face of the groove and the upper face of the inner groove wall that is shorter than a height of the outer groove wall extending between the inner bottom face of the groove and the upper face of the outer groove wall, wherein the bottom out surface of the at least one tray is supported directly against the upper surface of the inner groove wall of the immediately adjacent tray below the at least one tray and the tongue of the at least one tray is disposed within groove of the immediately adjacent tray below the at least one tray so that the tongue is entirely spaced apart from the at least one wall of the immediately adjacent tray below the at least one tray; and an adhesive disposed within the groove of the immediately adjacent tray below the at least one tray so as to bond the tongue of the at least one tray to the at least one wall of the immediately adjacent tray below the at least one tray.

6. The cell culturing device of claim 5, wherein the outer groove wall of the at least one tray is entirely spaced apart from the immediately adjacent tray above the at least one tray.

* * * * *